United States Patent [19]

Kirkpatrick et al.

[11] 4,097,264
[45] Jun. 27, 1978

[54] CHLORO-TERT.BUTYL-1,3,4-THIADIAZOLEUREA HERBICIDES AND USE TO COMBAT UNWANTED VEGETATION

[75] Inventors: Joel L. Kirkpatrick, Overland Park; Jr. Doyle, Leawood, both of Kans.

[73] Assignee: Gulf Oil Corporation, Pittsburgh, Pa.

[21] Appl. No.: 360,204

[22] Filed: May 14, 1973

[51] Int. Cl.$^2$ ............................................. A01N 9/12
[52] U.S. Cl. ................................. 71/90; 260/306.8 D
[58] Field of Search ..................... 71/90; 260/306.8 D

[56] References Cited

U.S. PATENT DOCUMENTS

| | | | |
|---|---|---|---|
| 3,669,982 | 6/1972 | Cebalo et al. | 260/306.8 D |
| 3,673,203 | 6/1972 | Miller | 260/306.8 D |
| 3,779,736 | 12/1973 | Doyle, Jr. | 71/90 |
| 3,803,164 | 4/1974 | Ji Ping Tao | 260/306.8 D |

OTHER PUBLICATIONS

Derwent Pat. Abst. — 69056s–c, Week S–43, 12/24/71.
Sato et al., Chem. Abst., vol. 72, 1970, 43685f.
Kubo et al., Chem. Abst., vol. 72, 1970, 53955h.

*Primary Examiner*—Catherine L Mills
*Attorney, Agent, or Firm*—Carl A. Cline

[57] ABSTRACT

Chloro and dichloro tert.butyl-1,3,4-thiadiazole-di- and trimethylurea compounds are extraordinarily phytotoxic compounds which are particularly useful for nonselectively combating unwanted vegetation.

2 Claims, No Drawings

CHLORO-TERT.BUTYL-1,3,4-THIADIAZOLEUREA HERBICIDES AND USE TO COMBAT UNWANTED VEGETATION

DESCRIPTION OF THE INVENTION

A few members of the class of thiadiazoleureas of the general structural formula

have been reported to have utility as herbicides, particularly compounds in which Y is trifluoromethyl, chloromethyl, bromoethyl and chloroethyl. In general the prior art compounds are either selective in their action, or if they are relatively non-selective, they fail to possess the high degree of non-selective toxicity which is necessary in order to be commercially competitive as so-called industrial herbicides. Less than a half-dozen specific compounds are in extensive commercial use for the purpose of keeping a plot of ground free of vegetation. This is a consequence of the number of requirements which a compound of this type must meet. Ordinarily both pre- and post-emergent efficacy are desired and the compound must have the ability to remain in place in the soil in sufficiently effective concentration so that the area requires treatment no more than once per year. Resistance to leaching, oxidation and attack by soil bacteria and fungi are necessary properties for commercial desirability.

We have discovered that unwanted vegetation may be effectively combated by the method which comprises the step of applying to the area in which the vegetation is unwanted an effective amount of a compound having the structural formula

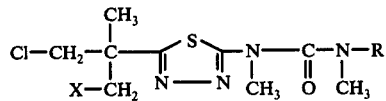

in which X represents H or Cl and R represents H or CH₃.

The herbicides which are suitable for use in the method of combating vegetation belong to a very small group, their outstanding phytotoxic properties being attributable to the presence of the highly branched chlorotert.butyl and dichlorotert.butyl substituents on the thiadiazole structure.

Preparation of the novel herbicides and use in the method of combating vegetation are illustrated in the following discussion and examples.

PREPARATION OF THE HERBICIDES

The novel herbicides may be prepared from purchased raw materials according to procedures which are specifically exemplified below.

Preparation of 2-methylamino-5-(β-chloro-α,α-dimethylethyl)-1,3,4-thiadiazole To a well stirred suspension of 125 g of 4-methylthiosemicarbazide and 165 g of β-chloropivalic acid in 500 ml of dioxane was added 186 g of phosphorus oxychloride at a rate which maintained the temperature below 60°. The reaction mixture was then heated at reflux until HCl evolution ceased (about 4 hrs). After cooling, the supernatant liquid was decanted from the plastic mass and 500 ml of water was added. With cooling, sodium hydroxide pellets were added until a pH of 10 was maintained. The resulting precipitate was collected, washed with water and air dried giving 216 g m.p. 91°-93°, (87%). Recrystallization from methylene chloride-ether gave the analytical sample, m.p. 93°-95°.

Anal. Calcd. for $C_7H_{12}ClN_3S$: C, 40.87; H, 5.88; N, 20.43. Found: C, 40.94; H, 5.90; N, 20.37.

Preparation of 2-methylamino-5-(α,α-bischloromethylethyl)-1,3,4-thiadiazole

To a stirred suspension of 34 g of 4-methylthiosemicarbazide in 50 ml of dioxane was added 60 g of α,α-bischloromethyl propionyl chloride, then heated to reflux temperature. Carefully 50 g of phosphorus oxychloride was added and heating continued until HCl evolution ceased. After cooling, the supernatant liquid was decanted from the viscous material that had separated, water was added and the mixture taken to a pH of 10 with sodium hydroxide pellets. No precipitate formed. The solution was extracted with chloroform, the extract was shaken with water then with saturated sodium chloride solution and was then dried over $Na_2SO_4$. The chloroform was removed at reduced pressure and the residue crystallized with a mixture of methylene chloride-petroleum ether to give 27.8 g, m.p. 105°-107° (36%). An analytical sample, m.p. 108°-109°, was prepared from methylene chloride-petroleum ether.

Anal. Calcd. for $C_7H_{11}Cl_2N_3S$: C, 35.01; H, 4.62; N, 17.50. Found: C, 35.31; H, 4.80; N, 17.66.

Preparation of 1,3-Dimethyl-3-[5-(β-chloro-α,α-dimethylethyl)-1,3,4-thiadiazol-2-yl]urea To a stirred suspension of 6.0 g of 2-methylamino-5-(β-chloro-α,α-dimethylethyl)-1,3,4-thiadiazole in 100 ml of benzene was added 2.0 g of methyl isocyanate. The mixture became homogenous upon heating to reflux temperature and reflux was maintained for 2 hrs. After cooling, the benzene was removed at reduced pressure and the precipitate collected, giving 7.4 g (95%), m.p. 159°-161°. An analytical sample was prepared from methylene chloride-ether, m.p. 160°-161°.

Anal. Calcd. for $C_9H_{15}ClN_4OS$: C, 41.14; H, 5.75; N, 21.32. Found: C, 41.04; H, 6.03; N, 21.34.

Preparation of 1,3-Dimethyl-3-[5-(α,α-bischloromethylethyl)-1,3,4-thiadiazol-2-yl]urea The urea compound was prepared by reacting methyl isocyanate with the corresponding thiadiazole according to the procedure described above, m.p. 150°-152°. Analytical sample recrystallized from methylene chloride-petroleum ether, m.p. 151°-153°.

Anal. Calcd. for $C_9H_{14}Cl_2N_4OS$: C, 36.37; H, 4.75; N, 18.85. Found: C, 36.60; H, 4.86; N, 18.85.

Preparation of 1,1,3-trimethyl-3-[5-(β-chloro-α,α-dimethylethyl)-1,3,4-thiadiazol-2-yl]urea To a solution of 50.0 g of 2-methylamino-5-(β-chloro-α,α-dimethylethyl)-1,3,4-thiadiazole in 300 ml of pyridine was added 46.0 g of dimethyl carbamyl chloride and the reaction heated at reflux temperature for 16 hrs. After cooling, the pyridine was removed on the rotary evaporator and water added to the residue. The reaction was extracted with ether which was shaken with water, saturated sodium chloride and dried over $Na_2SO_4$. The solvent was removed at reduced pressure giving 60 g of a viscous oil. Crystallization was effected using a mixture of ether-petroleum ether; wt. 34.5 g (52%), m.p. 80°–82°. Recrystallization from ether-petroleum ether gave the analytical sample, m.p. 82°–83°.

Anal. Calcd. for $C_{10}H_{17}ClN_4OS$: C, 43.39; H, 6.19; N, 20.24. Found: C, 43.09; H, 6.07; N, 19.98.

Combating Unwanted Vegetation

Post-emergent use of the herbicides to combat unwanted vegetation may be demonstrated by means of the procedure described below.

Post-Emergent Use

An aqueous dispersion of each active compound is prepared, for example, by combining 0.24 gram of the compound with about 2 ml of a solvent-emulsifier mixture (3 parts of a commercial polyoxyethylated vegetable oil emulsifier, one part xylene, one part kerosene) and then adding water, with stirring, to a final volume of 80 ml for the 1 lb per acre rate. Lower rates of application require more dilution so as to maintain constant spray volume. The species of plants on which each compound is to be tested are planted in disposable 12 in. × 10 in. greenhouse flats about 3 in. deep. Twelve days after emergence of the plants, one flat containing eleven species is sprayed at each rate with an aqueous dispersion of the active compound prepared as described above, at rates of 1 lb, ½ lb and ¼ lb of active compound per acre and at a spray volume of 40 gallons per acre. Approximately two weeks after the spray application the plants are observed and the results rated according to the following schedule.

DEGREE OF EFFECT

0 = no effect
1 = slight effect (observable, but no permanent injury)
2 = moderate effect (some plants died)
3 = severe effect (most of the plants died)
4 = maximum effect (all plants died)

Pre-emergent use of the herbicides to combat vegetation may be demonstrated by means of the procedure described below.

Pre-Emergent Use

A solution of each active compound is prepared by the method described above. Disposable expanded polystyrene trays about 2¼ inches deep and about one square foot in area are filled with soil, seeded and sprayed with the solution at the various rates of active chemical per acre of sprayed area. Twenty-eight days after seeding and treatment the plantings are examined and herbicidal effects are rated according to the schedule as described above.

Results of both post-emergent and pre-emergent use are tabulated below. The sums of the scores in the Last column of the table give a measure of overall efficacy of the group of relatively non-selective herbicides. In general, only one deficiency is clearly apparent and that is low efficacy on nutsedge. Low toxicity to nutsedge is a frequently observed property of highly phytotoxic, relatively non-selective herbicides and is believed to be indicative of unique biological and characteristics possessed by nutsedge species.

TABLE I

HERBICIDAL USE OF COMPOUNDS OF THE FORMULA $$Cl-CH_2-\underset{\underset{X-CH_2}{|}}{\overset{\overset{CH_3}{|}}{C}}-\overset{S}{\overset{\|}{C}}-\underset{N}{\overset{N}{\underset{\|}{\diagdown}}}\!\!\!\diagup\!\!\!\overset{N-C-N-R}{\underset{CH_3\ O\ CH_3}{|\ \ \ \ \ \ \ |}}$$

| COMPOUND X | R | APPLICATION TYPE AND RATE lb/A. | Pigweed (Amaranthus retroflexus) | Crabgrass (Digitaria sanguinalis) | Downy brome (Bromus inermis) | Nutsedge (Cyperus esculentis) | Peanut (Arachis hypogaea) | Cotton (Gossypium herbaceum) | Morningglory (Ipomea purpurea) | Barnyard grass (Echinochloa crusgalli) | Corn (Zea mays) | Grain Sorghum (Sorghum vulgare) | Shattercane (Sorghum bicolor) | Σ |
|---|---|---|---|---|---|---|---|---|---|---|---|---|---|---|
| H | H | Post 1 | 4 | 4 | 4 | 1 | 4 | 4 | 4 | 4 | 3 | 4 | 4 | 40 |
|   |   | Pre 1 | 4 | 4 | 4 | 0 | 2 | 4 | 4 | 1 | 1 | 4 | 4 | 35 |
|   |   | Post 2 | 4 | 4 | 4 | 0 | 1 | 4 | 4 | 3 | 2 | 4 | 4 | 32 |
|   |   | Pre 2 | 4 | 4 | 4 | 0 | 1 | 4 | 4 | 0 | 1 | 4 | 2 | 34 |
|   |   | Post 4 | 4 | 2 | 2 | 0 | 0 | 2 | 3 | 3 | 1 | 2 | 2 | 24 |
|   |   | Pre 4 | 4 | 3 | 3 | 1 | 4 | 4 | 4 | 3 | 1 | 2 | 2 | 23 |
| Cl | H | Post 1 | 4 | 4 | 3 | 0 | 3 | 4 | 4 | 2 | 2 | 4 | 4 | 31 |
|   |   | Pre 1 | 4 | 3 | 3 | 0 | 0 | 3 | 4 | 4 | 1 | 4 | 1 | 37 |
|   |   | Post 2 | 4 | 3 | 2 | 0 | 1 | 4 | 4 | 1 | 0 | 2 | 3 | 22 |
|   |   | Pre 2 | 4 | 1 | 1 | 0 | 0 | 1 | 3 | 0 | 0 | 0 | 0 | 27 |
|   |   | Post 4 | 0 | 0 | 0 | 2 | 3 | 4 | 1 | 0 | 0 | 0 | 0 | 14 |
|   |   | Pre 4 | 4 | 4 | 4 | 3 | 4 | 4 | 4 | 4 | 3 | 4 | 4 | 2 |
| H | CH₃ | Post 1 | 4 | 4 | 4 | 0 | 1 | 4 | 4 | 4 | 4 | 4 | 4 | 40 |
|   |   | Pre 1 | 4 | 4 | 4 | 0 | 2 | 4 | 4 | 4 | 3 | 3 | 3 | 43 |
|   |   | Post 2 | 4 | 4 | 3 | 0 | 0 | 4 | 4 | 4 | 3 | 4 | 4 | 34 |
|   |   | Pre 2 | 4 | 4 | 3 | 0 | 1 | 4 | 4 | 4 | 1 | 2 | 2 | 37 |
|   |   | Post 4 | 4 | 3 | 3 | 0 | 2 | 4 | 4 | 4 | 2 | 3 | 4 | 25 |
|   |   | Pre 4 | 4 | 3 | 4 | 0 | 1 | 4 | 4 | 4 | 3 | 3 | 4 | 33 |

TABLE II

COMPARATIVE TESTS OF PRIOR ART COMPOUNDS OF THE FORMULA $$F_3C-\underset{N-N}{\overset{S}{\bigvee}}-\underset{\underset{R'}{|}\ \underset{O}{||}\ \underset{H}{|}}{N-C-N-CH_3}$$

| COMPOUND R' | APPLICATION TYPE AND RATE (lb/A.) | Pigweed (Amaranthus retroflexus) | Crabgrass (Digitaria sanguinalis) | Downy brome (Cyperus inermis) | Nutsedge (cyperus esculentis) | Peanut (Arachis hypogaea) | Cotton (Gossypium herbaceum) | Morningglory (Ipomez purpurea) | Barnyard grass (Echinochloa crusgalli) | Corn (Zea mays) | Grain Sorghum (Sorghum vulgare) | Shattercane (Sorghum bicolor) | Σ |
|---|---|---|---|---|---|---|---|---|---|---|---|---|---|
| H | Post | 3 | 3 | 4 | 0 | 2 | 4 | 3 | 3 | 1 | 3 | 3 | 29 |
|  | Pre | 4 | 2 | 2 | 1 | 0 | 0 | 0 | 4 | 0 | 4 | 4 | 21 |
| CH₃ | Post | 4 | 3 | 4 | 0 | 2 | 4 | 3 | 2 | 0 | 1 | 1 | 24 |
|  | Pre | 4 | 4 | 4 | — | 0 | 4 | — | — | 1 | — | — |  |

Determination of an effective amount of herbicide to be used in the method is partially a matter of personal choice, depending upon whether absence of vegetation is desired for a long or a short period of time. It can be seen from the tabulated data that application of as little as 1 lb/A is sufficient to combat vegetation in the immediate future. As the concentration declines over a period of time under the effects of wind and water erosion and decomposition from various causes, the effect will diminish. Ordinarily it is preferred to select an effective amount which is considerably more than sufficient for the immediate future and will leave adequate residue in the soil so as to remain effective for several months. The herbicides employed in the method of this invention are not believed to be soil sterilants, as forms of life, other than plants are not affected in any readily apparent manner.

We claim:

1. The method of combating unwanted vegetation comprising the step of applying to the area in which the vegetation is unwanted an effective amount of a compound having the structural formula

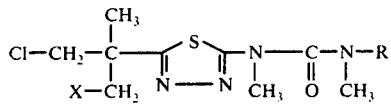

in which X is H and R is $CH_3$.

2. The herbicidal composition which consists essentially of 1,1,3-trimethyl-3-[5-(2-chloro-1,1-dimethylethyl)-1,3,4-thiadiazol-2-yl]urea and an inert carrier.

* * * * *

UNITED STATES PATENT AND TRADEMARK OFFICE
CERTIFICATE OF CORRECTION

PATENT NO. : 4,097,264
DATED : Jun. 27, 1978
INVENTOR(S) : Joel L. Kirkpatrick, William C. Doyle, Jr.

It is certified that error appears in the above—identified patent and that said Letters Patent are hereby corrected as shown below:

On the title page the Inventors are listed as Joel L. Kirkpatrick, Overland Park; Jr. Doyle, Leawood, both of Kans.

They should be listed as Joel L. Kirkpatrick, Overland Park; William C. Doyle, Jr., Leawood, both of Kans.

The formula in Column 1, Line 10 which reads

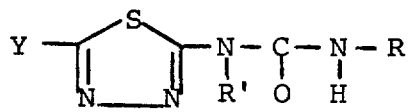   should read   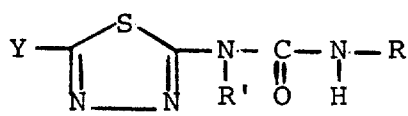

Signed and Sealed this

Sixteenth Day of January 1979

[SEAL]

Attest:

RUTH C. MASON
Attesting Officer

DONALD W. BANNER
Commissioner of Patents and Trademarks